United States Patent
Nishihara

(10) Patent No.: US 9,435,730 B2
(45) Date of Patent: Sep. 6, 2016

(54) IMAGE INFORMATION OBTAINING APPARATUS AND CONTROL METHOD FOR SAME

(75) Inventor: Hiroshi Nishihara, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 664 days.

(21) Appl. No.: 13/810,802

(22) PCT Filed: Jul. 8, 2011

(86) PCT No.: PCT/JP2011/003922
§ 371 (c)(1),
(2), (4) Date: Jan. 17, 2013

(87) PCT Pub. No.: WO2012/014391
PCT Pub. Date: Feb. 2, 2012

(65) Prior Publication Data
US 2013/0121106 A1 May 16, 2013

(30) Foreign Application Priority Data
Jul. 27, 2010 (JP) .................................. 2010-168161

(51) Int. Cl.
*G01N 29/06* (2006.01)
*G01N 21/17* (2006.01)
(Continued)

(52) U.S. Cl.
CPC .......... *G01N 21/1702* (2013.01); *A61B 5/0073* (2013.01); *A61B 5/0095* (2013.01);
(Continued)

(58) Field of Classification Search
CPC .............. A61B 5/0095; A61B 5/0073; A61B 5/14546; A61B 8/587; G01N 29/06; G01N 29/0672; G01N 29/0654; G01N 21/1702; G01N 21/1708

USPC ............................................................ 367/7
See application file for complete search history.

(56) References Cited

U.S. PATENT DOCUMENTS 4,466,443 A * 8/1984 Utsugi ........................... 600/463
6,106,469 A   8/2000 Suzuki et al. ................. 600/443
(Continued)

FOREIGN PATENT DOCUMENTS

JP   S55-073250   6/1980
JP   7-178081     7/1995
(Continued)

OTHER PUBLICATIONS

Ku et al, "Thermoacoustic and Photoacoustic Tomography of THick Biological Tissues Toward Brest Imaging", Technology in Cancer Research and Treatment, vol. 4, No. 5, Oct. 2005.*

(Continued)

*Primary Examiner* — Ian J Lobo
(74) *Attorney, Agent, or Firm* — Fitzpatrick, Cella, Harper & Scinto

(57) ABSTRACT

An image information obtaining apparatus having: a light source; a transducer which detects an acoustic wave and converts the acoustic wave to an electrical signal; a signal processing unit which generates image data, using the electrical signal; and a memory unit which stores a reference acoustic signal produced by the transducer detecting an acoustic wave generated when light is irradiated from the light source onto a phantom having acoustic parameters and optical parameters substantially the same as an object and converting the acoustic wave to an electrical signal, wherein the transducer produces an object acoustic signal by converting the acoustic wave, generated when light is irradiated onto an object from the light source, to an electrical signal; and the signal processing unit subtracts the reference acoustic signal from the object acoustic signal and generates image data from the signal resulting from this subtraction.

18 Claims, 8 Drawing Sheets

(51) Int. Cl.
*A61B 5/00* (2006.01)
*A61B 8/00* (2006.01)
*A61B 5/145* (2006.01)

(52) U.S. Cl.
CPC ........... *A61B5/14546* (2013.01); *A61B 8/587* (2013.01); *A61B 2560/0228* (2013.01); *G01N 29/06* (2013.01); *G01N 29/0654* (2013.01)

(56) References Cited

U.S. PATENT DOCUMENTS

| | | | |
|---|---|---|---|
| 6,216,025 | B1 | 4/2001 | Kruger ........................... 600/407 |
| 2001/0044580 | A1* | 11/2001 | Pellegretti et al. ........... 600/437 |
| 2004/0039379 | A1 | 2/2004 | Viator et al. ...................... 606/9 |
| 2005/0085725 | A1* | 4/2005 | Nagar et al. ................... 600/437 |
| 2005/0234319 | A1* | 10/2005 | Mandelis et al. .............. 600/407 |
| 2009/0005685 | A1* | 1/2009 | Nagae et al. ................... 600/459 |
| 2009/0069653 | A1 | 3/2009 | Yoshida et al. ............... 600/323 |
| 2009/0069674 | A1 | 3/2009 | Masumura et al. ........... 600/425 |
| 2009/0069676 | A1 | 3/2009 | Nishihara ...................... 600/437 |
| 2009/0069685 | A1 | 3/2009 | Nishihara et al. ............ 600/443 |
| 2009/0198128 | A1* | 8/2009 | Fukutani et al. .............. 600/437 |
| 2010/0041987 | A1* | 2/2010 | Manohar et al. .............. 600/437 |
| 2010/0053618 | A1 | 3/2010 | Nakajima et al. ............. 356/432 |
| 2011/0239766 | A1 | 10/2011 | Nakajima et al. ............... 73/587 |
| 2013/0165765 | A1 | 6/2013 | Nishihara ...................... 600/407 |
| 2013/0231549 | A1 | 9/2013 | Yamamoto et al. ........... 600/407 |

FOREIGN PATENT DOCUMENTS

| | | |
|---|---|---|
| JP | 2000-107177 | 4/2000 |
| JP | 2002-536041 | 10/2002 |
| JP | 2009-082450 | 4/2009 |
| JP | 2010-075681 | 4/2010 |
| JP | 2010-136887 | 6/2010 |
| WO | WO 00/045707 | 8/2000 |
| WO | WO 2010/005109 | 1/2010 |

OTHER PUBLICATIONS

M. Xu et al., "Photoacoustic Imaging in Biomedicine", *Review of Scientific Instruments* 77, 041101 (Apr. 17, 2006).

J.J. Niederhauser et al., "Combined Ultrasound and Optoacoustic System for Real-Time High-Contrast Vascular Imaging in Vivo", *IEEE Transactions on Medical Imaging*, vol. 24, No. 4, pp. 436-440 (Apr. 2005).

Office Action issued on Sep. 16, 2014, in Japanese Patent Application 2010-168161, with translation.

* cited by examiner

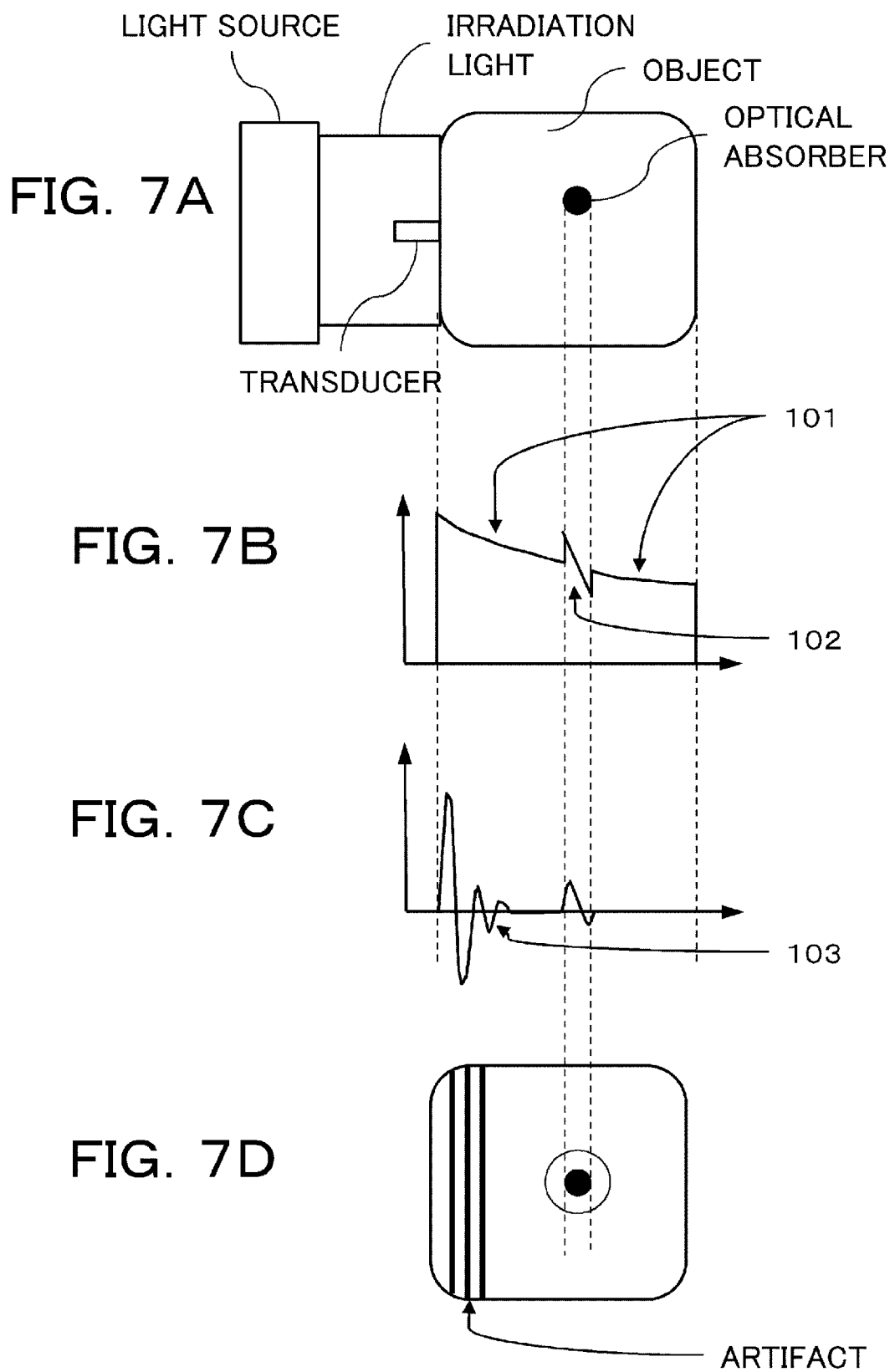

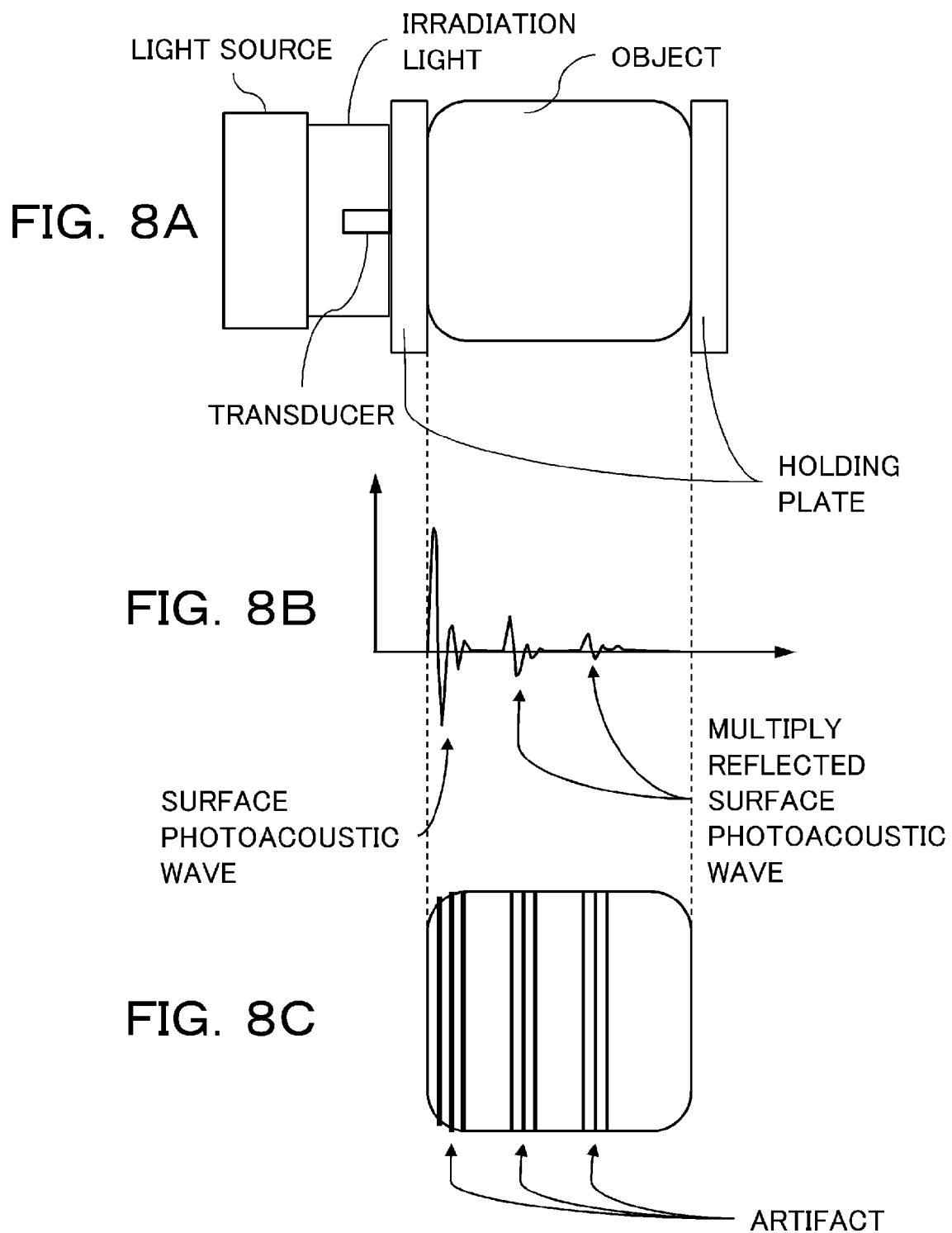

IMAGE INFORMATION OBTAINING APPARATUS AND CONTROL METHOD FOR SAME

TECHNICAL FIELD

The present invention relates to an image information obtaining apparatus and a control method for same.

BACKGROUND ART

In the field of medicine, there has been active research into optical imaging apparatuses which irradiate light onto a living organism, which is an object under inspection, from a light source, such as a laser, and create an image of information inside the living organism obtained on the basis of the incident light. One example of optical imaging technology of this kind is Photoacoustic Tomography (PAT). In PAT, pulse light generated from a light source is irradiated onto a living organism, and the living tissue absorbs the pulse light which propagates and diffuses inside the organism and generates an acoustic wave (typically, an ultrasound wave), which is detected. The mechanism producing this photoacoustic wave is called the photoacoustic effect. An acoustic wave generated by the photoacoustic effect is called a photoacoustic wave.

A site under inspection, such as tumor, often has a higher light energy absorption rate compared to the surrounding tissue, and therefore absorbs a larger amount of light than the surrounding tissue and swells momentarily. The acoustic wave generated by this swelling action is detected by a transducer to obtain a reception signal. By mathematically analyzing the reception signal, it is possible to create an image of the acoustic pressure distribution of the photoacoustic wave produced by the photoacoustic effect inside the object. On the basis of photoacoustic image data obtained in this way, it is possible to obtain a distribution of optical characteristics, and in particular, a distribution of the absorption coefficient, inside the living organism. This information can be used for quantitative measurement of specific substances in the object, for example, glucose or hemoglobin contained in blood. In recent years, in use of the PAT, preclinical research which creates images of blood vessels of small animals, and clinical research which applies this principle to diagnosis of breast cancer, and the like, has been pursued actively.

FIG. 7A shows a schematic diagram of an image information obtaining apparatus which creates images of the interior of an object by PAT, and FIG. 7B shows a sound pressure-time curve of a photoacoustic wave arriving at the transducer shown in FIG. 7A. Furthermore, FIG. 7C shows a reception signal-time curve detected by the transducer, and FIG. 7D shows a photoacoustic image. The portion indicated by 101 in FIG. 7B is the signal amplitude caused by the photoacoustic wave occurring due to light absorption by the object, and is principally constituted by a low frequency component. Since the photoacoustic wave signal produced by light absorption in the object rises in the vicinity of the surface of the object, then in the present invention, the photoacoustic wave occurring due to absorption of light by the object is called a surface photoacoustic wave. On the other hand, the portion 102 is the signal amplitude caused by the photoacoustic wave produced by a locally situated optical absorber inside the object such as a tumor, and is principally constituted by a high frequency component. Since a sound pressure-time waveform is detected by a transducer of limited bandwidth having low sensitivity at low frequency, then a reception signal-time waveform such as that shown in FIG. 7C is obtained. The portion 103 in FIG. 7C is the transient response (signal amplitude) which occurs when the surface acoustic wave is detected by a transducer of limited bandwidth.

When the interior of an object is imaged by using the reception signal-time waveform in FIG. 7C and a photoacoustic image is acquired, the signal amplitude caused by the surface photoacoustic wave appears as an artifact such as that shown in FIG. 7D. Therefore, if an optical absorber, such as a tumor, is present nearer to the transducer side than the example shown in FIG. 7A, then the signal amplitude 102 caused by the photoacoustic wave produced by the optical absorber is concealed by the signal amplitude 103 caused by the surface photoacoustic wave. As a result of this, there is a problem in that an image of an optical absorber, such as a tumor, is concealed in the artifact, when imaging is performed.

Moreover, there are cases where a holding plate is provided in an image information obtaining apparatus which uses a photoacoustic effect. The holding plate is a mechanism which fixes an object on the apparatus. The purpose of providing this mechanism is to prevent movement of the object and change in the measurement position during measurement, and to enable imaging in a deep part of the object by making the object thinner by compression. FIG. 8A shows a schematic drawing of an image information obtaining apparatus of this kind; FIG. 8B shows a reception signal-time waveform and FIG. 8C shows a photoacoustic image.

If a holding plate is provided as in FIG. 8A, a multiply reflected surface photoacoustic wave is detected by the transducer, due to multiple reflection inside the holding plate. In other words, a waveform corresponding to 101 in FIG. 7 is reflected by the light source side surface of the holding plate, and is then reflected again by the object side surface, and detected by the transducer. In this case, a transient response similar to that described above is produced. This is the signal amplitude caused by the multiply reflected surface photoacoustic wave and is detected as shown in FIG. 8B. If a photoacoustic image is acquired using the reception signal including the multiply reflected surface photoacoustic wave, then an image such as that shown in FIG. 8C is obtained, and similarly to the case of the surface photoacoustic wave, there is a problem in that an image of a tumor, or the like, is concealed by an artifact produced by the multiply reflected surface photoacoustic wave.

Another issue similar to that of a surface photoacoustic wave described above in an image information obtaining apparatus using a photoacoustic effect is the appearance of artifacts in an ultrasound diagnostic apparatus. More specifically, multiple reflection of the transmitted ultrasound wave is repeated at intermediate objects between the transducer and the object, for example, the acoustic window, the object compression plate, or the like, and this manifests itself as multiple echo artifacts in the image.

A technique for reducing artifacts caused by multiple reflection of this kind in an ultrasound echo method is disclosed in Patent Literature 1. In the apparatus described in Patent Literature 1, a reference acoustic signal including a multiply reflected ultrasound wave is previously acquired by measurement using a phantom (artificial living organism), and the reference acoustic signal is then subtracted from the signal obtained by measuring the object.

Furthermore, Patent Literature 2 discloses a method for removing multiple echo produced by an acoustic window constituting an ultrasound diagnostic apparatus. In Patent Literature 2, multiple echo extracted by averaging a plurality of reception signals that have been received is subtracted from the reception signals so as to remove the multiple echo.

Moreover, Patent Literature 3 discloses a method for removing a multiply reflected image produced by a plate for compressing an object, which forms part of a medical imaging apparatus that displays an ultrasound diagnostic image. In Patent Literature 3, image data representing a plurality of ultrasound images is generated and a multiply reflected image is extracted from the generated image data. A multiply reflected image is removed by subtracting an extracted multiply reflected image from the image data of the object.

CITATION LIST

Patent Literature

[PTL 1]
Japanese Patent Application Publication No. H7-178081
[PTL 2]
Japanese Patent Application Publication No. 2000-107177
[PTL 3]
Japanese Patent Application Publication No. 2009-082450

SUMMARY OF INVENTION

Technical Problem

In the apparatus described in Patent Literature 1, a reference acoustic signal including a multiply reflected ultrasonic wave is previously acquired by measurement using a phantom, and the reference acoustic signal is then subtracted from the signal obtained by measuring the object. The phantom used to acquire this reference acoustic signal is disclosed as follows. More specifically, the phantom is made of a uniform substance having a surface layer with an acoustic impedance similar to that of living skin (1.5 to 1.6*10$^6$ kg/m$^2$sec), and having an interior with an acoustic impedance similar to that to the surface of living skin, whereby there are no acoustic impedance reflections.

However, when using a photoacoustic effect, even if the phantom described above is employed, the intensity of the surface photoacoustic wave produced by the phantom described above is different to the surface photoacoustic wave produced by the object and therefore the artifact cannot be removed.

Furthermore, in an image information obtaining apparatus using a photoacoustic effect, photoacoustic waves are detected at a plurality of different positions. By measuring the photoacoustic waves simultaneously in a plurality of different positions, the measurement time can be shortened, and therefore it is common to use an array transducer in which a plurality of elements are aligned. Light is irradiated so as to illuminate an object region on the front surface of the array transducer. In this case, the irradiated light generally has a spatial intensity distribution.

The amplitude of the photoacoustic wave produced by the photoacoustic effect is directly proportional to the light intensity distribution. Therefore, the surface photoacoustic wave has a spatial sound pressure distribution which is proportional to the spatial intensity distribution of the light irradiated onto the surface of the object. Similarly, the multiply reflected surface photoacoustic wave has a spatial sound pressure distribution. Spatial sound pressure distribution of this kind is a particular feature of an image information obtaining apparatus based on a photoacoustic effect, which generates and detects photoacoustic waves by using light having a spatial intensity distribution.

The array transducer detects a surface photoacoustic wave having the spatial sound pressure distribution described above, and therefore the amplitude of the surface photoacoustic wave detected by each of the elements constituting the transducer is respectively different. Therefore, when using the method described in Patent Literature 2, a plurality of reception signals having different amplitudes are averaged, and therefore the amplitude of the multiple echo which is extracted does not necessarily coincide with the amplitude of the multiple echo in the reception signals. Therefore, it is difficult to subtract the multiple echo adequately. More specifically, the method described in Patent Literature 2 has beneficial effects in an ultrasound diagnostic apparatus in which the amplitude of the detected multiple echo is uniform, but has a problem in that sufficient beneficial effects are difficult to achieve in application to an image information obtaining apparatus using a photoacoustic effect which has a spatial sound pressure distribution. Furthermore, the method described in Patent Literature 3 requires image data which represents a plurality of ultrasound images, and therefore it is necessary to make a plurality of measurements. Hence, there is a problem in that the measurement time is long.

Moreover, Patent Literature described above relates to an ultrasound echo apparatus. In an ultrasound echo method, a reflected ultrasonic wave produced when an ultrasonic pulse emitted from the ultrasonic wave oscillator in a probe is reflected once by the surface of a member constituting the apparatus can be distinguished from the echo produced by the object which is under measurement, and therefore does not form noise. Only a multiply reflected ultrasonic wave which has been reflected two or more times has a possibility of being superimposed on the echo produced by the object under measurement, and thus forming noise. In this way, with an ultrasound echo method, only a multiply reflected ultrasonic wave which is reflected two or more times forms noise, whereas an apparatus based on a photoacoustic effect differs from this in that a reflected ultrasonic wave which has been reflected one or more times forms noise.

In this way, the patent literatures described above disclose a method of removing multiply reflected ultrasonic waves in an ultrasound echo method, but as yet there has been no disclosure about surface photoacoustic waves in an apparatus which uses a photoacoustic effect or a method for removing multiply reflected surface photoacoustic waves.

The present invention was devised in view of these circumstances, an object thereof being to provide an image information obtaining apparatus which is capable of obtaining photoacoustic image data having reduced artifacts.

Solution to Problem

This invention provides an image information obtaining apparatus, comprising:
a light source;
a transducer which detects an acoustic wave and converts the acoustic wave to an electrical signal;
a signal processing unit which generates image data, using the electrical signal;
a memory unit which stores a reference acoustic signal produced by the transducer detecting an acoustic wave generated when light is irradiated from the light source onto a phantom having acoustic parameters and optical parameters substantially the same as an object and converting the acoustic wave to an electrical signal, wherein the transducer produces an object acoustic signal by converting the acoustic wave, generated when light is irradiated onto an object from the light source, to an electrical signal, and the signal processing unit subtracts the reference acoustic signal from the object acoustic signal and generates image data from the signal resulting from this subtraction.

This invention also provides an image information obtaining apparatus, comprising:

a light source;

a transducer which detects an acoustic wave and converts the acoustic wave to an electrical signal;

a signal processing unit which generates image data, using the electrical signal;

a memory unit which stores image data generated by the signal processing unit from a reference acoustic signal produced by the transducer detecting an acoustic wave generated when light is irradiated from the light source onto a phantom having acoustic parameters and optical parameters substantially the same as an object, and converting the acoustic wave to an electrical signal, wherein the transducer produces an object acoustic signal by converting the acoustic wave, generated when light is irradiated onto an object from the light source, to an electrical signal; and the signal processing unit generates image data from the object acoustic signal, and subtracts image data generated from the reference acoustic signal, from the image data generated from the object acoustic signal.

This invention also provides a control method for an image information obtaining apparatus having: a light source; a transducer which detects an acoustic wave and converts the acoustic wave to an electrical signal; a memory unit; and a signal processing unit which generates image data, the control method comprising:

a step of irradiating light from the light source onto a phantom having acoustic parameters and optical parameters substantially the same as an object;

a step of detecting by the transducer detects an acoustic wave generated from the phantom which has absorbed light, and converting the acoustic wave to an electrical signal, and moreover storing the electrical signal in the memory unit as a reference acoustic signal;

a step of irradiating light onto an object from a light source;

a step of detecting by the transducer an acoustic wave generated from the object which has absorbed light, and converting the acoustic wave to an electrical signal, and moreover storing the electrical signal in the memory unit as an object acoustic signal; and a step of subtracting by the signal processing unit the reference acoustic signal from the object acoustic signal and generating image data from the signal resulting from this subtraction.

This invention also provides a control method for an image information obtaining apparatus having: alight source; a transducer which detects an acoustic wave and converts the acoustic wave to an electrical signal; a memory unit; and a signal processing unit which generates image data, the control method comprising:

a step of irradiating light from the light source onto a phantom having acoustic parameters and optical parameters substantially the same as an object;

a step of producing by the transducer a reference acoustic signal by detecting an acoustic wave generated from the phantom which has absorbed light and converting the acoustic wave to an electrical signal;

a step generating by the signal processing unit image data from the reference acoustic signal;

a step of storing the image data generated from the reference acoustic signal in the memory unit;

a step of irradiating light onto an object from a light source;

a step of producing by the transducer an object acoustic signal by converting an acoustic wave, generated when light is irradiated onto an object from the light source, to an electrical signal;

a step of generating by the signal processing unit image data from the object acoustic signal; and a step of subtracting by the signal processing unit image data generated from the reference acoustic signal, from image data generated from the object acoustic signal.

Advantageous Effects of Invention

According to the present invention, it is possible to provide an image information obtaining apparatus capable of obtaining photoacoustic image data having reduced artifacts.

Further features of the present invention will become apparent from the following description of exemplary embodiments with reference to the attached drawings.

BRIEF DESCRIPTION OF DRAWINGS

FIGS. 7A to 7D are schematic drawings for describing the formation of artifacts; and FIGS. 8A to 8C are schematic drawings of an image information obtaining apparatus having a holding plate.

DESCRIPTION OF EMBODIMENTS

A desirable mode for carrying out the present invention is described below with reference to the drawings. The dimensions, materials, shapes and relative positions, and the like, of the constituent parts described below should be changed appropriately depending on the composition and various conditions of the apparatus to which the invention is applied, and it is not intended to limit the scope of the invention to the description given below. Furthermore, the present invention may also be interpreted as a control method by which an information processing apparatus, or the like, controls the image information obtaining apparatus described below.

Example 1

In Example 1, an example of the composition of the image information obtaining apparatus to which the present invention is applied will be described.

Figure 1A:
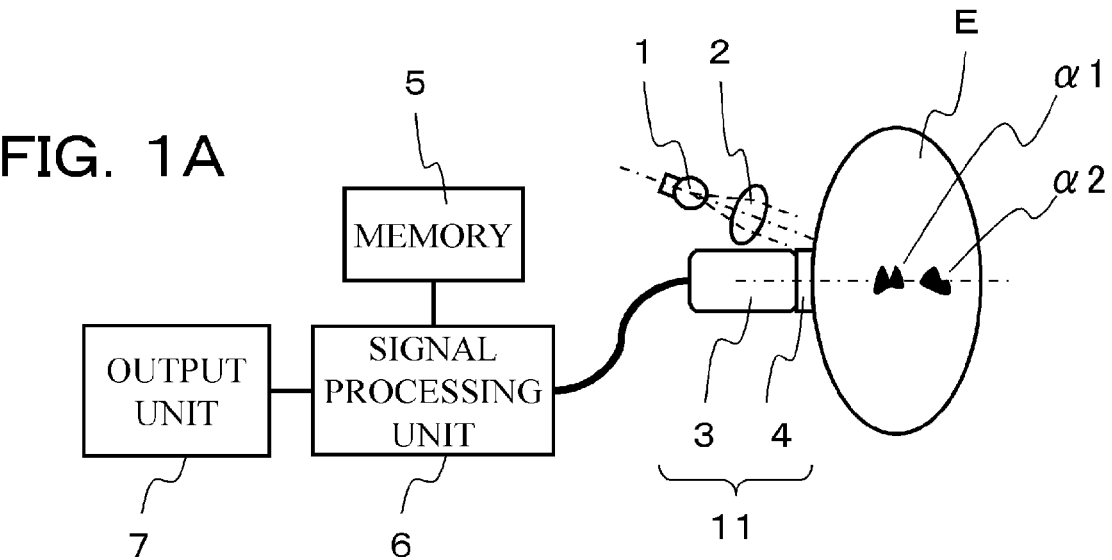
FIGS. 1A and 1B are schematic drawings for describing the composition of an image information obtaining apparatus according to Example 1 of the present invention.

FIG. 1A shows a schematic diagram illustrating the composition of the image information obtaining apparatus according to the present example. The image information obtaining apparatus in FIG. 1A comprises a light source 1, an optical system 2, a transducer 3, an acoustic matching member 4, a memory 5, a signal processing unit 6, an output unit 7 and an acoustic wave detection probe 11. In FIG. 1A, E denotes an object of inspection. The object E is living tissue, such as a breast, for example. The object E includes internal tissue a1 and a2. It is possible to envisage that the internal tissue is an optical absorber, such as a tumor, for example.

Below, the details of each constituent element are described.

Light source 1 is a light source which emits nanosecond order pulse light of a specific wavelength that is irradiated onto the object E. The wavelength of the light emitted by the light source 1 is set to a wavelength corresponding to the absorption spectra of the water, fat, protein, oxygenated hemoglobin, reduced hemoglobin, and the like, which constitute the living tissue. For example, since water, which is the main component of internal living tissue, has low absorption, light is transmitted well through the water, and therefore an appropriate wavelength range is 600 to 1500 nm, where the spectra of fats, oxygenated hemoglobin and reduced hemoglobin show characteristic features.

Figure 2:
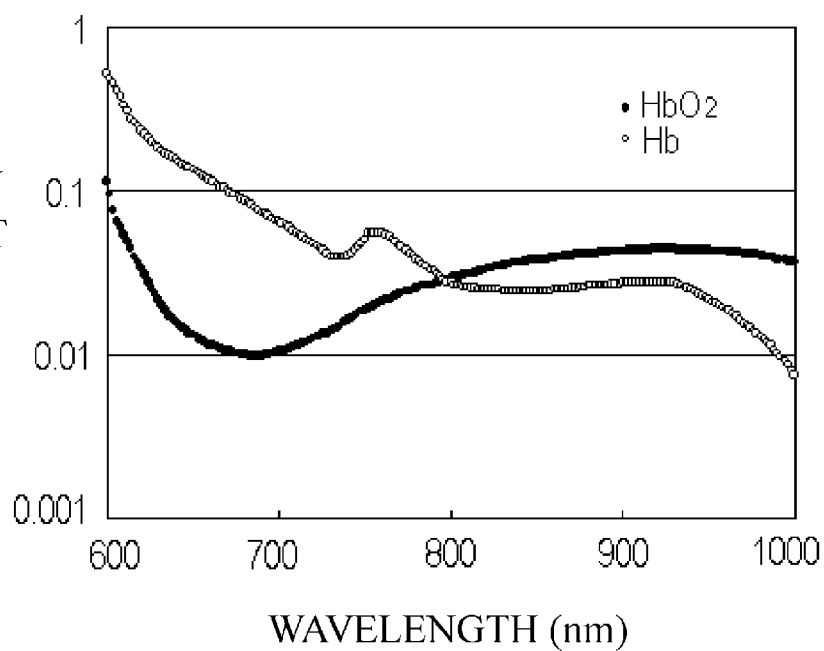
FIG. 2 is a diagram showing absorption spectra of $HbO_2$ and Hb.

Moreover, it is known that if a cancerous tumor, or the like, grows in living tissue, then new blood vessels form and the consumption of oxygen increases. A method of assessing the formation of new blood vessels and increase in oxygen consumption in this way is to use the characteristic features of the absorption spectra of oxygenated hemoglobin ($HbO_2$) and reduced hemoglobin (Hb). FIG. 2 shows absorption spectra of $HbO_2$ and Hb in the wavelength range of 600 to 1000 nm.

In an image information obtaining apparatus, the concentration of Hb and $HbO_2$ contained in the blood inside the living tissue is measured from the absorption spectra of Hb and $HbO_2$ at a plurality of wavelengths. The concentrations of Hb and $HbO_2$ are measured at a plurality of positions and image data of a concentration distribution is created, thereby making it possible to distinguish a region where new blood vessels have been formed in the living tissue. Furthermore, it is also possible to calculate the oxygen saturation from the concentrations of Hb and $HbO_2$ and to distinguish a region where the oxygen consumption has increased, from the oxygen saturation. Spectral information relating to Hb and $HbO_2$ which has been measured by an image information obtaining apparatus in this way can be used for diagnostic purposes.

Suitable specific examples of the light source 1 are a semiconductor laser which produces different wavelengths, or a variable wavelength laser, or the like. The optical system 2 is set so as to guide the liquid emitted from the liquid source 1, to the object E. The optical system 2 is constituted by an optical fiber and a lens. The light emitted from the light source 1 is expanded by the optical system 2, passed through an acoustic matching member 4, and guided to the surface of the object E. An irradiation apparatus is formed by the light source 1 and the optical system 2.

The acoustic wave detection probe 11 is constituted by a transducer 3 having a piezoelectric effect which converts pressure change caused by a received acoustic wave to an electrical signal, and an acoustic matching member 4. In the present specification, the signal obtained by converting an acoustic wave produced by a photoacoustic effect into an electric signal by means of a transducer 3, is taken as an acoustic signal. The transducer 3 may be an array type of transducer including an alignment of a plurality of elements which receive an acoustic wave and convert the acoustic wave to an electrical signal. It is known that, if the size of a cancerous tumor, or the like, becomes 2 to 3 mm or more, due to the development of the tumor, then the formation of new blood vessels increases. Therefore, for the transducer 3, it is appropriate to use a material suited to detection of acoustic waves of 0.5 MHz to several 10 MHz produced by an optical absorber no more than several mm in size, due to a photoacoustic effect. More specifically, it is possible to use a piezoelectric ceramic material, typically PZT (lead zirconate titanate), or a polymer piezoelectric material, typically PVDF (polyvinylidene fluoride), or the like. Furthermore, elements other than piezoelectric elements may be used. For example, it is possible to use a transducer in which elements of an electrostatic capacitance type, such as CMUT (Capacitive Micromachined Ultrasonic Transducers), or the like, are arranged.

Furthermore, in many cases, there is a large difference in acoustic impedance between the transducer 3 and the object E. In this case, there is greater reflection at the interface where the transducer 3 makes contact with the object E and it is difficult to transmit the acoustic wave generated by the photoacoustic effect efficiently to the transducer 3. Therefore, an acoustic matching member 4 which is made of a material having an intermediate acoustic impedance between that of the object E and the transducer 3 and which has a thickness set to ¼ of the wavelength of the acoustic wave is provided. Examples of the material constituting the acoustic matching member 4 are epoxy resin, quartz glass, urethane rubber, and the like. It is also possible to envisage a composition where an acoustic matching member is not disposed, and a composition in which the acoustic matching member is integrated with a transducer (or a probe including a transducer).

The memory 5 is a memory unit that stores a reference acoustic signal, which is described hereinafter. For the memory 5, it is possible to use a data recording apparatus, such as an optical disk, a magnetic disk, a semiconductor memory, a hard disk, or the like. The signal processing unit 6 is connected to the transducer 3, the memory 5 and the output unit 7. The signal processing unit 6 has a function for subtracting a reference acoustic signal previously stored in the memory 5, from an object acoustic signal obtained by measuring the object E. Furthermore, the signal processing unit 6 also has a function for generating image data for displaying the signal processing results on the output unit 7. The output unit 7 is a display for displaying the signal processing results from the signal processing unit 6. It is possible to use a display device, such as a liquid crystal display, a CRT, an organic EL display, or the like, for the output unit 7.

Figure 1B:
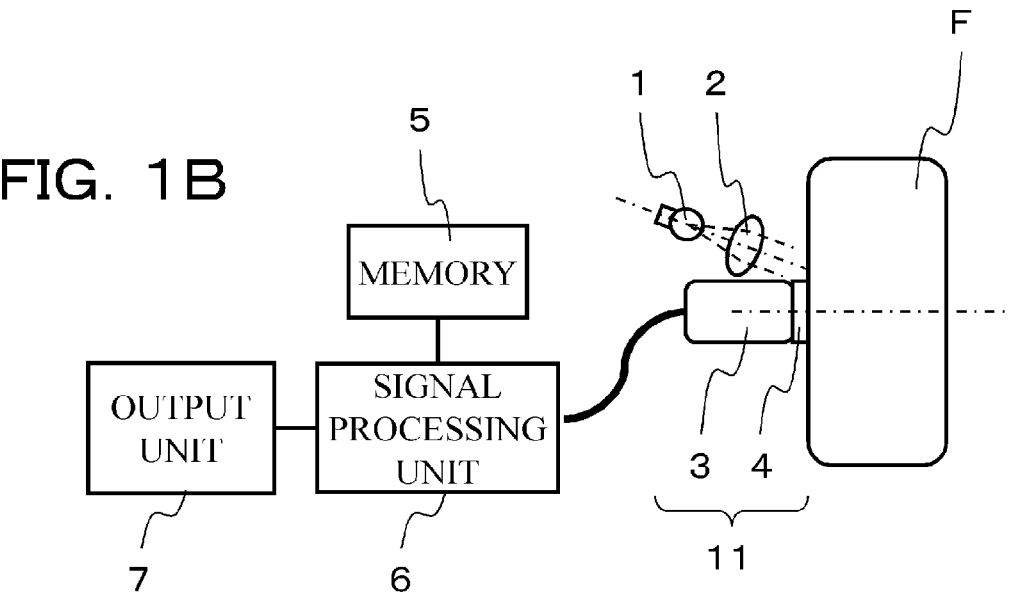

FIG. 1B shows a schematic diagram of the acquisition of a reference acoustic signal. A phantom F is provided instead of the object E in FIG. 1A. The other constituent elements are the same as in FIG. 1A, and description thereof is omitted here.

The phantom F has an acoustic impedance (acoustic parameter), and optical absorption properties and optical scattering properties (optical parameters) which are substantially equal to those of the object E. The phantom F may be regarded as an artificial living organism which simulates an object. For example, the acoustic impedance should be set to 1.5 to $1.6*10^6$ kg/m$^2$sec. Furthermore, the optical absorption properties and the optical scattering properties are set to different values depending on the wavelength of the light emitted by the light source 1. It is possible to use a commonly known material in respect of the optical absorption properties and the optical scattering properties of skin. For example, for light in the wavelength range of no less than 700 nm and no more than 1100 nm, the light scattering coefficient should be set to no less than 0.45 mm$^{-1}$ and no more than 2.8 mm$^{-1}$, and the light absorption coefficient should be set to be no less than 0.001 mm$^{-1}$ and no more than 0.03 mm$^{-1}$. Moreover, it is desirable if the light scattering coefficient is no less than 0.45 mm$^{-1}$ and no more than 1.2 mm$^{-1}$, and if the light absorption coefficient is no less than 0.005 mm$^{-1}$ and no more than 0.015 mm$^{-1}$, since optical characteristics closer to those of a living organism are obtained. In particular, since the typical light absorption coefficient ma of breast tissue at a wavelength of 1064 nm is 0.01 mm$^{-1}$ and the light scattering coefficient ms' is 0.9 mm$^{-1}$, then values close to these should be set.

In the apparatus shown in FIG. 1B, pulse light emitted from the light source 1 is expanded by the optical system 2 and guided to the surface of the phantom F. The light arriving at the phantom F is scattered at the surface and the interior of the phantom F. A portion of the scattered light is reflected by the probe, transmitted by the acoustic matching member 4 again, and then arrives at the surface of the transducer 3 which is in contact with the acoustic matching member 4.

In this case, surface photoacoustic waves based on the respective optical absorption properties are generated by a photoacoustic effect at the phantom F, the acoustic matching member 4, and the surface of the transducer 3, where the light reaches. Furthermore, when these surface photoacoustic waves propagate, they are reflected at the respective surfaces of the phantom F, the acoustic matching member 4 and the transducer 3, and multiply reflected surface photoacoustic waves is generated.

These acoustic waves are detected by the transducer 3 and are converted to an acoustic signal which is an electrical signal. In the present example, the reference acoustic signal is an acoustic signal obtained when the phantom F is measured. The result acquired for the reference acoustic signal is sent to the signal processing unit 6 connected to the transducer 3, and is stored in the memory 5 by the signal processing unit 6 and also displayed on the output unit 7.

Figure 3A:
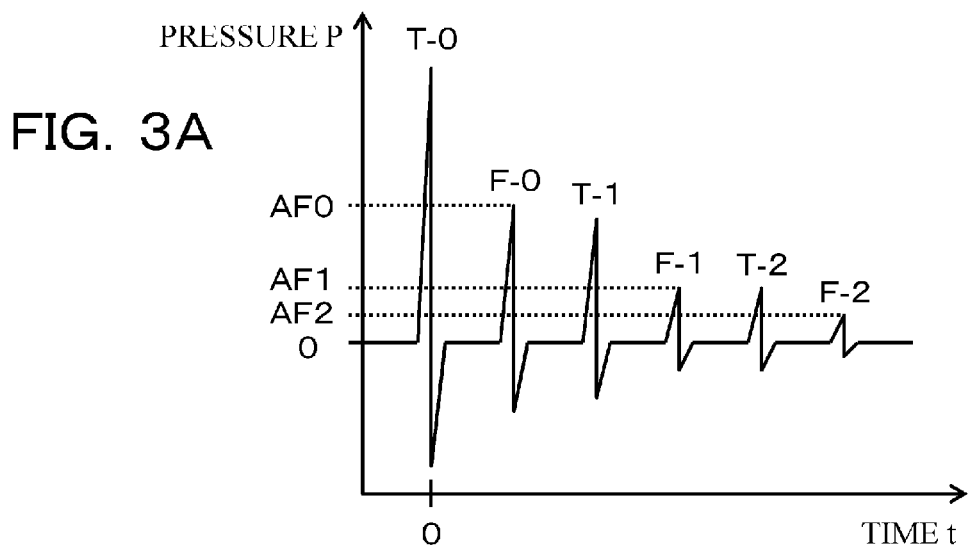
FIGS. 3A to 3C are diagrams showing various acoustic signal according to Example 1.

FIG. 3A shows a reference acoustic signal which is displayed on the output unit 7 when a phantom is measured by the method described above. In this figure, the horizontal axis indicates time t, and the vertical axis indicates the pressure converted from the acoustic signal.

T-0 is the signal amplitude due to the surface photoacoustic wave produced by a photoacoustic effect at the contact surface between the transducer 3 and the acoustic matching member 4 when pulse light is irradiated. F-0 is the signal amplitude due to the acoustic wave which arrives at the transducer 3 when a surface photoacoustic wave is generated by a photoacoustic effect at the contact surface between the acoustic matching member 4 and the phantom F when pulse light is irradiated, and the surface photoacoustic wave propagates through the acoustic matching member 4.

T-1 is the signal amplitude due to a multiply reflected surface photoacoustic wave which arrives at the transducer 3 after the surface photoacoustic wave T-0 has propagated through the acoustic matching member 4 and has been reflected once at the interface between the acoustic matching member 4 and the phantom F. T-2 is a signal amplitude due to a multiply reflected surface photoacoustic wave which arrives at the transducer 3 after the acoustic wave at T-1 has been reflected once at the interface between the transducer 3 and the acoustic matching member 4, has propagated in the acoustic matching member 4, and has been reflected a second time at the interface between the acoustic matching member 4 and the phantom F. Although not shown in the drawings, thereafter, T-3, T-4, and so on, are signal amplitudes due to multiply reflected surface photoacoustic waves.

F-1 is a signal amplitude of a multiply reflected surface photoacoustic wave which arrives at the transducer 3 after the surface photoacoustic wave at F-0 has been reflected once at the interface between the transducer 3 and the acoustic matching member 4, has propagated in the acoustic matching member 4, and has been reflected a first time at the interface between the acoustic matching member 4 and the phantom F. F-2 is a signal amplitude of a multiply reflected surface photoacoustic wave which arrives at the transducer 3 after the acoustic wave at F-1 has been reflected a second time at the interface between the transducer 3 and the acoustic matching member 4, has propagated in the acoustic matching member 4, and has been reflected a second time at the interface between the acoustic matching member 4 and the phantom F. Although not shown in the drawings, thereafter, F-3, F-4, and so on, are signal amplitudes due to multiply reflected surface photoacoustic waves.

Next, a case where the reference acoustic signal is subtracted from the object acoustic signal obtained by measuring the object E will be described.

In the apparatus shown in FIG. 1A, pulse light emitted from the light source 1 is expanded by the optical system 2, transmitted through the acoustic matching member 4 and guided to the surface of the object E. The light arriving at the object E is scattered by the surface and the interior of the object E. A portion of the scattered light is reflected by the probe, transmitted by the acoustic matching member 4 again, and then arrives at the surface of the transducer 3 which is in contact with the acoustic matching member 4.

In this case, an acoustic wave based on the optical absorption properties of the internal tissue is produced by a photoacoustic effect inside the object E. Furthermore, similarly to when acquiring the reference acoustic signal, surface photoacoustic waves based on the respective optical absorption properties are generated by a photoacoustic effect at the object E, the acoustic matching member 4, and the surface of the transducer 3, where the light reaches. Furthermore, when these surface photoacoustic waves propagates, they are reflected at the respective surfaces of the object E, the acoustic matching member 4 and the transducer 3, and multiply reflected surface photoacoustic waves are generated.

These acoustic waves are detected by the transducer 3 and are converted to an acoustic signal which is an electrical signal. In the present specification, the object acoustic signal is an acoustic signal obtained when the object E is measured. The result acquired for the object acoustic signal is sent to the signal processing unit 6 connected to the transducer 3, and is stored in the memory 5 by the signal processing unit 6.

Figure 3B:
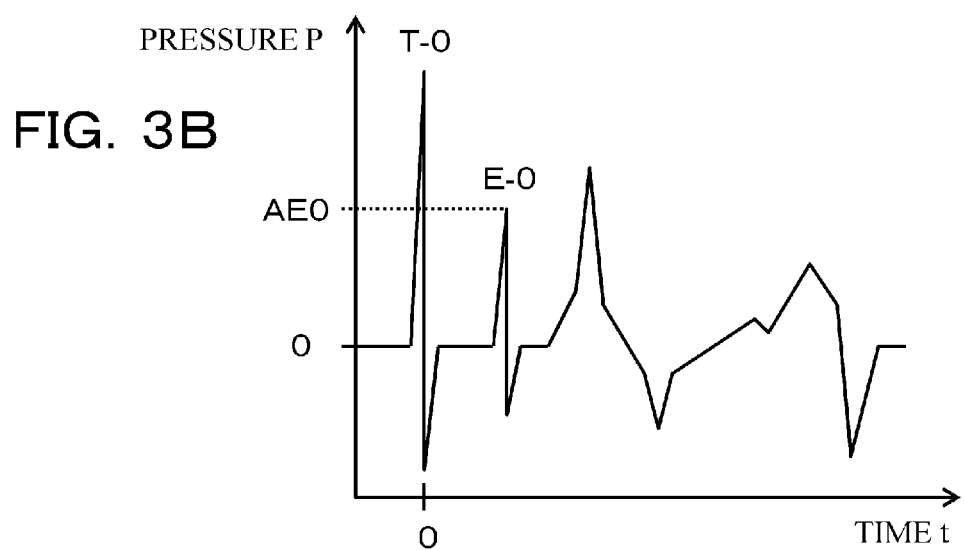

FIG. 3B shows an object acoustic signal stored in the memory 5.

T-0 is the signal amplitude of a surface photoacoustic wave at the contact surface between the transducer 3 and the acoustic matching member 4, similarly to that shown in FIG. 3A. E-0 is the signal amplitude of the acoustic wave which arrives at the transducer 3 when a surface photoacoustic wave is generated by a photoacoustic effect at the contact surface between the acoustic matching member 4 and the object E when pulse light is irradiated, and the surface photoacoustic wave propagates through the acoustic matching member 4.

The acoustic waves generated after F-0 are a synthesis of an acoustic wave generated by a photoacoustic effect in the internal tissue of the object E and the multiply reflected surface photoacoustic waves T-1, T-2, . . . , F-1, F-2, . . . , described in FIG. 3A.

The signal processing unit 6 is an apparatus which subtracts a reference acoustic signal previously stored in the memory 5 from the object acoustic signal, and generates image data using the signal resulting from this subtraction (differential acoustic signal). The output unit 7 displays this image data. Furthermore, it can also display the differential acoustic signal before it is converted into image data.

Figure 3C:
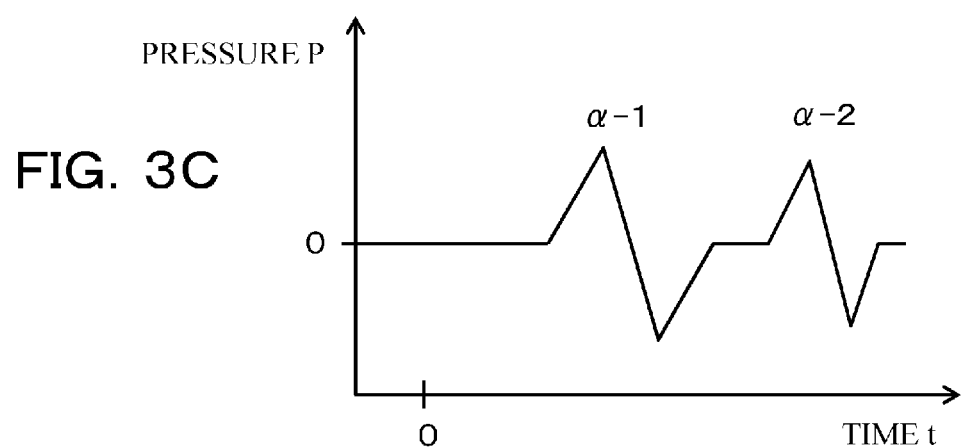

FIG. 3C shows a differential acoustic signal obtained by subtracting the reference acoustic signal from the object acoustic signal displayed on the output unit 7. The N-shaped waveforms a-1 and a-2 shown in FIG. 3C represent a state where artifacts have been reduced in the signals from the internal tissue a1 and a2 of the object E shown in FIG. 1A.

As described above, in the image information obtaining apparatus according to the present example, it is possible to reduce the effects of surface photoacoustic waves and multiply reflected surface photoacoustic waves, by subtracting a reference acoustic signal from the object acoustic signal. By using an acoustic signal of this kind, it is possible to obtain photoacoustic image data having reduced artifacts.

Modification Example

Figure 4A:
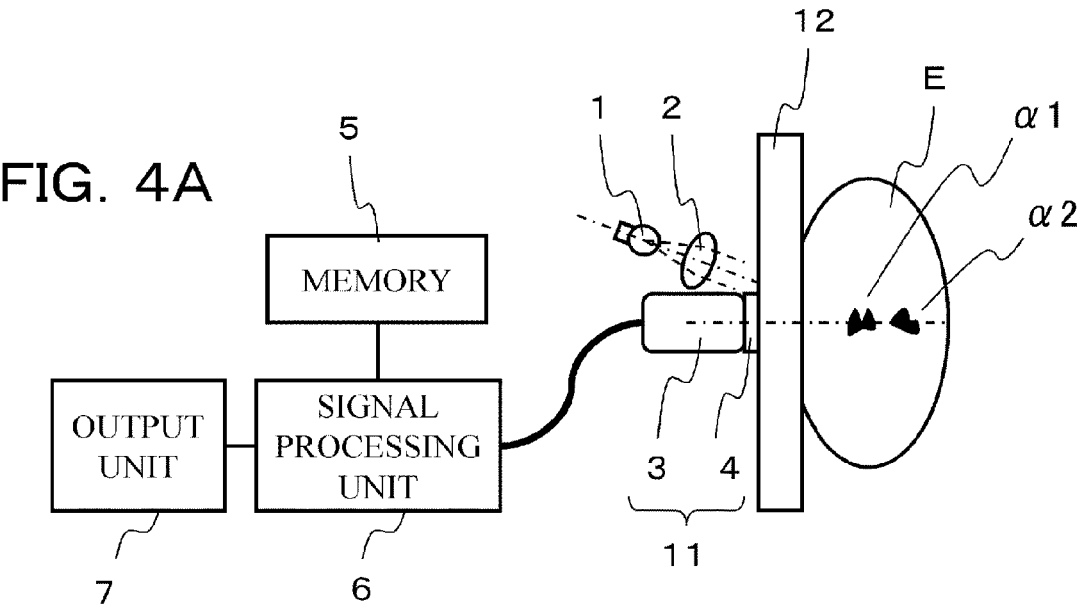
FIGS. 4A and 4B are schematic drawings for describing a modification example of an image information obtaining apparatus according to Example 1.
Figure 4B:
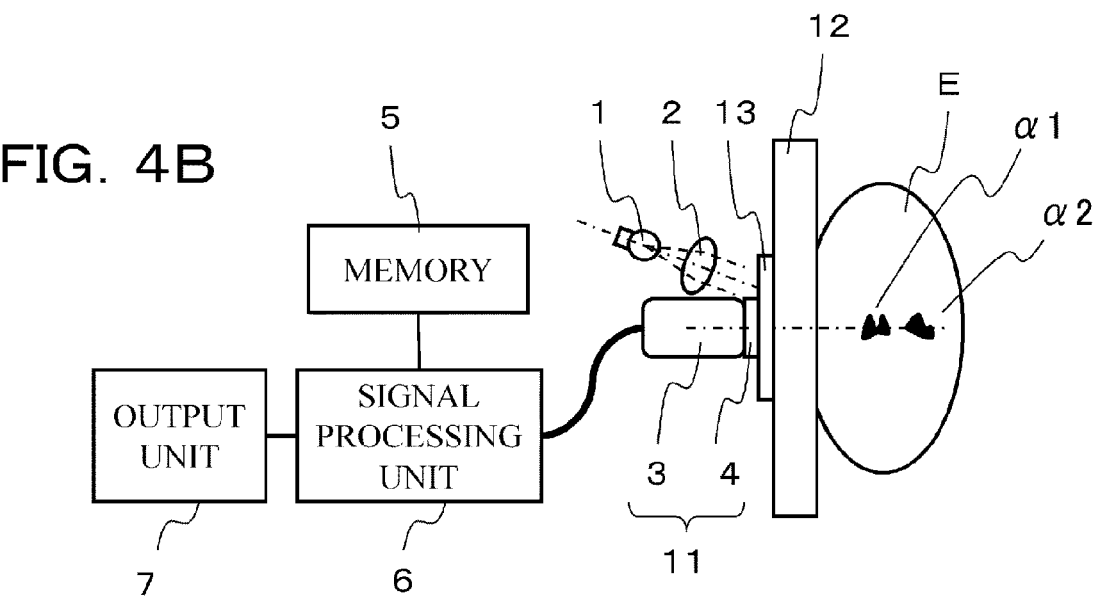

Furthermore, FIGS. 4A and 4B show modification examples of an image information obtaining apparatus according to the present example. Below, the description centers on the constituent elements which differ from FIG. 1.

In the example shown in FIG. 4A, a second acoustic matching member 12 for holding an object E is provided between the acoustic matching member 4 and the object E. The second acoustic matching member 12 is a flat plate which holds the object E by making contact with the object E, and furthermore, the second acoustic matching member 12 has high transmissivity and low attenuation with respect to acoustic waves generated by a photoacoustic effect, and high transmissivity and low attenuation with respect to light emitted by the light source 1. Examples of the material constituting the acoustic matching member 4 are quartz glass, polymethyl pentene polymer, polycarbonate, acrylic, or the like.

In the example shown in FIG. 4B, a third acoustic matching member 13 is provided in a gap between the acoustic matching member 4 and the second acoustic matching member 12. The third acoustic matching member 13 is provided for the purpose of acoustic impedance matching between the acoustic matching member 4 and the second acoustic matching member 12. The third acoustic matching member 13 has high transmissivity and low attenuation with respect to acoustic waves produced by the photoacoustic effect and high transmissivity and low attenuation with respect to light emitted by the light source 1. For the material constituting the third acoustic matching member 13, it is possible to use water, castor oil, acoustic wave inspection gel, or the like.

Even if a holding member and matching agent are added, as shown in FIG. 4A and FIG. 4B, it is still possible to remove the effects of surface photoacoustic waves and multiply reflected surface photoacoustic waves by means of a similar method to that described above. In this case, by performing measurement using a phantom, a reference signal including the effects of surface photoacoustic waves produced at the surface of the holding member and the matching agent is obtained, saved in a memory and used for signal processing. By using an acoustic signal of this kind, it is possible to obtain photoacoustic image data having reduced artifacts.

Furthermore, in the present example, a case was described where a previously acquired reference signal is subtracted from an object signal, but it is possible to obtain similar beneficial effects by acquiring and subtracting a reference signal after acquiring an object signal.

Example 2

There are individual differences between the optical absorption properties and the optical scattering properties of an object E. It might be possible to prepare individually matched phantoms for the phantom F shown in Example 1, but if the number of persons being measured is high, then costs rise and a large amount of time is also required to acquire the reference acoustic signal. Example 2 relates to the composition of an image information obtaining apparatus which is able to correct for disparities caused by these individual differences by using a phantom F having average values for the optical absorption properties and the optical scattering properties.

Below, the method of correcting individual differences in the optical absorption properties and the optical scattering properties in the present example is described. The composition of the apparatus used here is similar to that of Example 1.

Similarly to Example 1, a reference acoustic signal of the phantom F shown in FIG. 3A is obtained. In this case, the signal intensity of the surface photoacoustic wave at F-0 is AF0, the signal intensity of the acoustic wave at F-1 is AF1, and the signal intensity of the acoustic wave at F-2 is AF2.

Moreover, similarly to Example 1, an object acoustic signal for the object E shown in FIG. 3B is acquired. In this case, the signal intensity of the surface photoacoustic wave at E-0 is AE0. E-0 is a surface photoacoustic wave generated by a photoacoustic effect at the contact surface between the acoustic matching member 4 and the object E, and therefore if AF0 and AE0 are equal when compared with each other, the optical absorption properties and the optical scattering properties of the phantom F and the object E are the same.

In other words, it is possible to correct differences in the optical absorption properties and the optical scattering properties of the phantom F and the object E by correcting the signal intensity AF0 of the reference acoustic signal at F-0 to the intensity AE0.

The acoustic impedance of the phantom F and the object E is taken to be substantially equal, and AF1 shown in FIG. 3A is corrected to AF1*(AE0/AF0), and AF2 is corrected to AF2*(AE0/AF0). Similarly, thereafter, values are corrected to AF3*(AE0/AF0), AF4*(AE0/AF0), and so on. By performing correction in this way, it is possible to obtain a corrected reference acoustic signal based on the optical absorption properties and the optical scattering properties of the object E.

The signal processing unit 6 generates the corrected reference acoustic signal described above and stores this corrected reference acoustic signal in the memory 5. In this way, the signal processing unit 6 functions as a corrected acoustic signal generation unit for generating a corrected reference acoustic signal. The signal processing unit 6 generates image data using a differential acoustic signal obtained by subtracting the corrected reference acoustic signal stored previously in the memory 5 from the object acoustic signal. The output unit 6 displays this image data, as an image.

As described above, in the image information obtaining apparatus according to the present embodiment, the object acoustic signal and the reference acoustic signal are compared and a coefficient for use in correction is determined. By then subtracting the corrected reference acoustic signal from the object acoustic signal, it is possible to remove the effects of the surface photoacoustic waves and multiply reflected surface photoacoustic waves based on the optical absorption properties and the optical scattering properties of the object E. By using an acoustic signal of this kind, it is possible to obtain photoacoustic image data having reduced artifacts.

Example 3

An example of the composition of an image information obtaining apparatus which removes the effects of multiply reflected surface photoacoustic waves using cross-sectional image data is now described with reference to FIG. 5A. The constituent members labeled with the same reference numbers in FIG. 1A have the same function as those described above.

Figure 5A:
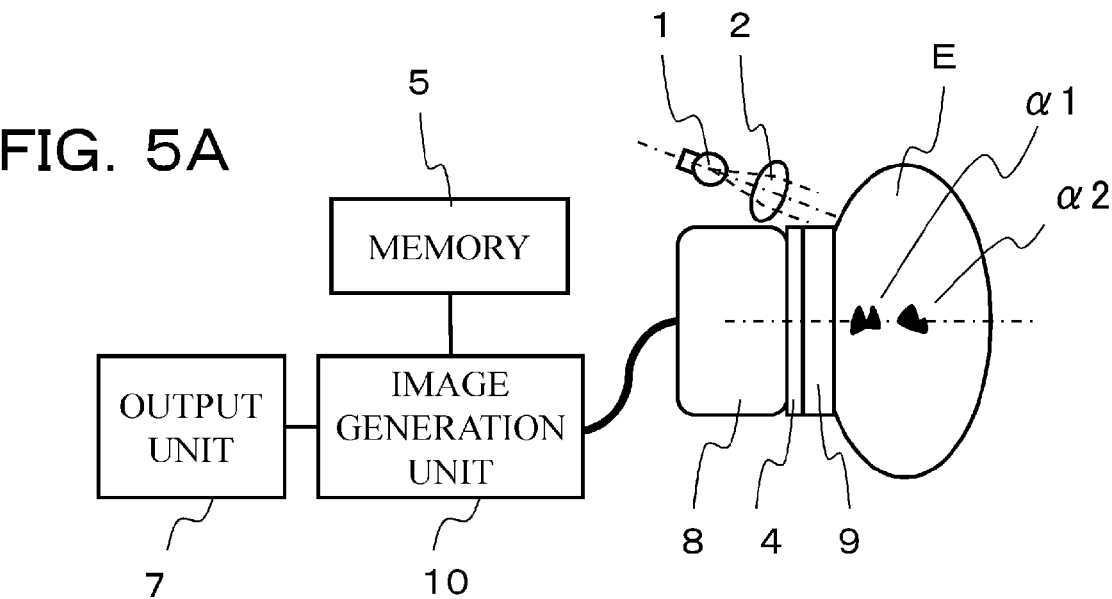
FIGS. 5A and 5B are schematic drawings for describing the composition of an image information obtaining apparatus according to Example 3 of the present invention.

The apparatus shown in FIG. 5A includes a one dimensional array transducer 8, an acoustic lens 9, and an image generation unit 10. The one dimensional array transducer 8 is formed by a one dimensional arrangement of piezoelectric elements which were described with respect to the transducer 3. A signal for a desired position is obtained by a Sum And Delay Beamforming method, from the plurality of acoustic signals obtained from the plurality of piezoelectric elements.

The acoustic lens 9 has a focal distance inside the object E, and high transmissivity and low permittivity with respect to acoustic waves produced by a photoacoustic effect, similarly to the acoustic matching member 4. The material constituting an acoustic lens is desirably a material having an intermediate acoustic impedance between the object E and the piezoelectric elements, for example, a silicone rubber or polymer resin material, or the like. If the acoustic lens is made of a material in which the speed of sound is slower than the speed of sound in the object E, then the lens has a convex shape, and the focal distance is determined by the curvature of the convex surface, while the focal size and focal depth are determined by the focal distance and the lens diameter. In the present embodiment, an acoustic lens is used, but it is also possible to use piezoelectric elements having a concave surface. Furthermore, similarly to Example 1, it is also possible to use an electrostatic capacitance type of element, or the like.

The image generation unit 10 is a signal processing unit having a function of generating two dimensional cross-sectional image data from an acoustic signal. The image generation unit 10 stores generated data in the memory 5, similarly to the signal processing unit 6 described in Example 1. Furthermore, the image generation unit 10 also has a function of subtracting reference image data from the object image data described below.

Figure 5B:
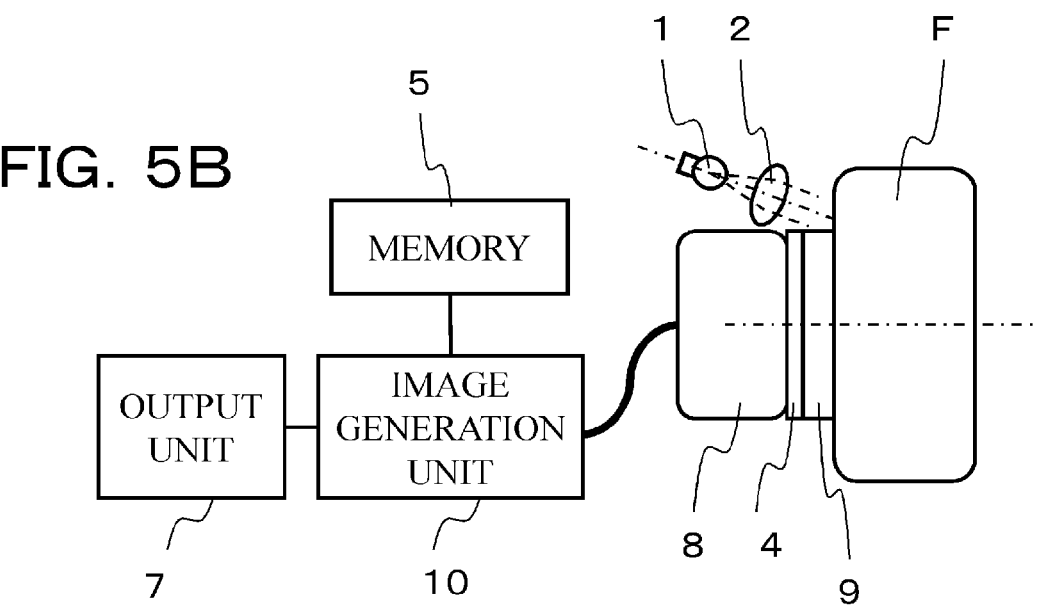

FIG. 5B shows the acquisition of reference image data. A phantom F is provided instead of the object E in FIG. 5A. The phantom F may use a phantom similar to that described in relation to Example 1.

In the apparatus shown in FIG. 5B, pulse light emitted from the light source 1 is expanded by the optical system 2 and guided to the surface of the phantom F from the vicinity of the side face of the acoustic lens 9. The light arriving at the phantom F is scattered at the surface and the interior of the phantom F. A portion of the scattered light is reflected by the probe and arrives at the acoustic lens 9 and the one dimensional array transducer 8.

In this case, surface photoacoustic waves based on the respective optical absorption properties are generated by a photoacoustic effect at the phantom F, the acoustic lens 9, and the surface of the one dimensional array transducer 8, where the light reaches. Furthermore, when these surface photoacoustic wave propagate, they are reflected at the respective surfaces of the phantom F, the acoustic lens 9 and the one dimensional array transducer 8, and multiply reflected surface photoacoustic waves are generated. These acoustic waves are detected by the one dimensional array transducer 8 and are converted to an acoustic signal which is an electrical signal.

The acoustic signal is supplied to the image generation unit 10 connected to the one dimensional array transducer 8, and two dimensional cross-sectional image data is generated by the image generation unit 10. In the present specification, the image data obtained by measuring the phantom F is taken as reference image data. The reference image data is stored in the memory 5 by the image generation unit 10.

Figure 6A:
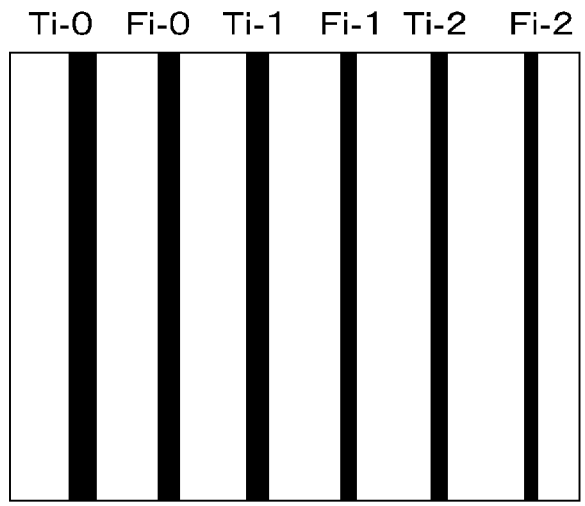
FIGS. 6A to 6C are diagrams showing various images according to Example 3.

FIG. 6A is a reference image displayed on the output unit 7.

The stripe pattern Ti-0 in FIG. 6A is an image produced by a surface photoacoustic wave generated by a photoacoustic effect at the contact surface between the one-dimensional array transducer 8 and the acoustic lens 9 when pulse light is irradiated. In order to simplify the description, in the present embodiment, no consideration is given to the thickness of the acoustic matching member 4, but if a surface photoacoustic wave occurs at the surface of the acoustic matching member, then this can be handled similarly to other contact surfaces. The stripe pattern Fi-0 is an image due to the acoustic wave which arrives at the one-dimensional array transducer 8 when a surface photoacoustic wave is generated by a photoacoustic effect at the contact surface between the acoustic lens 9 and the phantom F when pulse light is irradiated, and the surface photoacoustic wave propagates through the acoustic lens 9.

The stripe pattern Ti-1 is an image due to a multiply reflected surface photoacoustic wave which arrives at the transducer 3 after the surface photoacoustic wave at Ti-0 has propagated through the acoustic lens 9 and has been reflected once at the interface between the acoustic matching member 9 and the phantom F. The stripe pattern Ti-2 is an image produced by a multiply reflected surface photoacoustic wave. More specifically, an acoustic wave at Ti-1 propagates through the acoustic lens 9 after being reflected once at the interface between the one dimensional array transducer 8 and the acoustic lens 9, and then reaches the one dimensional array transducer 8 after being reflected for a second time at the interface between the acoustic lens 9 and the phantom F. Although not shown in the drawings, thereafter, there are also images Ti-3, Ti-4, and so on, due to multiply reflected surface photoacoustic waves.

The stripe pattern Fi-1 is an image produced by a multiply reflected surface photoacoustic wave. More specifically, a surface photoacoustic wave at Fi-0 propagates through the acoustic lens 9 after being reflected once at the interface between the one dimensional array transducer 8 and the acoustic lens 9, and then reaches the one dimensional array transducer 8 after being reflected for a first time at the interface between the acoustic lens 9 and the phantom F.

The stripe pattern Fi-2 is an image produced by a multiply reflected surface photoacoustic wave. More specifically, the surface photoacoustic wave at Fi-1 propagates through the acoustic lens 9 after being reflected for a second time at the interface between the one dimensional array transducer 8 and the acoustic lens 9, and then reaches the one dimensional array transducer 8 after being reflected for a second time at the interface between the acoustic lens 9 and the phantom F. Although not shown in the drawings, thereafter, there are also images Fi-3, Fi-4, and so on, due to multiply reflected surface photoacoustic waves.

Next, a case where the reference image data is subtracted from the object image data obtained by measuring the object E will be described.

In the apparatus shown in FIG. 5A, pulse light emitted from the light source 1 is expanded by the optical system 2 and guided to the surface of the object E in the vicinity of the side face of the acoustic lens 9. The light arriving at the object E is scattered by the surface and the interior of the object E. A portion of the scattered light is reflected by the probe and arrives at the acoustic lens 9 and the one dimensional array transducer 8.

In this case, an acoustic wave based on the optical absorption properties of the internal tissue is produced by a photoacoustic effect inside the object E. Furthermore, similarly to when acquiring the reference image data, surface photoacoustic waves based on the respective optical absorption properties are generated by a photoacoustic effect at the object E, the acoustic lens 9, and the surface of the one dimensional array transducer 8, where the light reaches. Furthermore, when these surface photoacoustic waves propagate, they are reflected at the respective surfaces of the object E, the acoustic lens 9 and the one dimensional array transducer 8, and multiply reflected surface photoacoustic waves are generated. These acoustic waves are detected by the one dimensional array transducer 8 and are converted to an acoustic signal which is an electrical signal. The acoustic signal is supplied to the image generation unit 10 connected to the one dimensional array transducer 8, and two dimensional cross-sectional image data is generated by the image generation unit 10. In the present specification, the image data obtained by measuring the object E is taken as object image data. The object image data is stored in the memory 5 by the image generation unit 10.

Figure 6B:
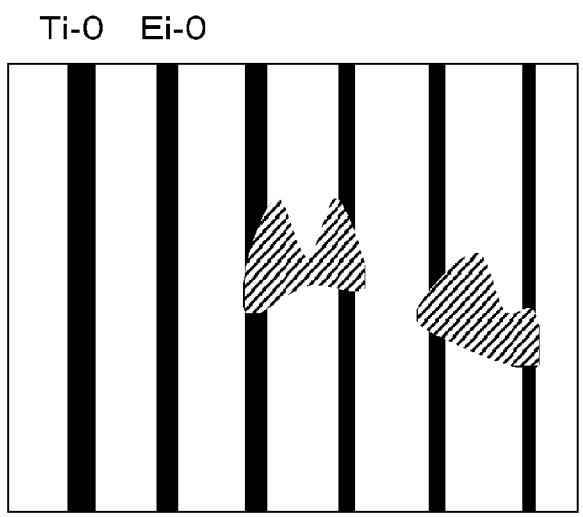

FIG. 6B is an object image displayed on the output unit 7.

The stripe pattern Ti-0 is an example of imaging using the composition shown in FIG. 5A. The stripe pattern Ei-0 is an image due to the acoustic wave which arrives at the one dimensional array transducer 8, when a surface photoacoustic wave is generated by a photoacoustic effect at the contact surface between the acoustic lens 9 and the object E when pulse light is irradiated, and the surface photoacoustic wave propagates through the acoustic lens 9.

The stripe patterns apart from the stripe patterns Ti-0 and Ei-0 are a synthesis of an acoustic wave produced by a photoacoustic effect in the internal tissue of the object E and the images Ti-1, Ti-2, . . . , Fi-1, Fi-2, . . . , caused by multiply reflected surface photoacoustic waves illustrated in FIG. 5A.

The image generation unit 10 which forms the signal processing unit outputs the result of subtracting the reference image data previously stored in the memory 5 from the object acoustic image data (differential image data), to the output unit 7, and the output unit 7 displays the differential image.

Figure 6C:
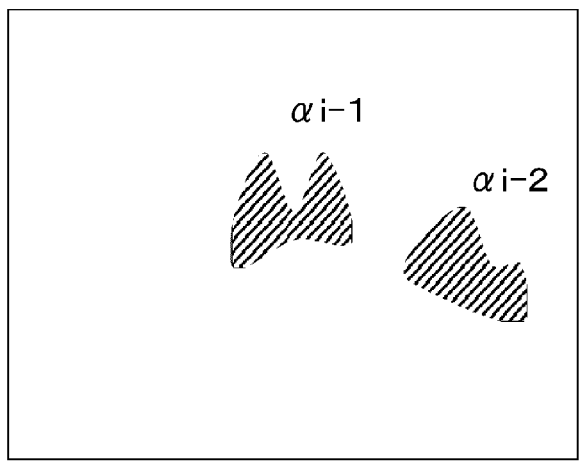

FIG. 6C is a differential image obtained by subtracting reference image data from object image data, which is displayed on the output unit 7. ai-1 indicates an acoustic wave from internal tissue a1 of the object E shown in FIG. 5A and ai-2 indicates an acoustic wave from internal tissue a2.

As described above, in the image information obtaining apparatus according to the present example, it is possible to reduce the effects of surface photoacoustic waves and multiply reflected surface photoacoustic waves, by subtracting reference image data from the object image data. By using an acoustic signal of this kind, it is possible to obtain photoacoustic image data having reduced artifacts.

In the present embodiment, cross-sectional image data is obtained by using a one dimensional array transducer, but it is also possible to obtain cross-sectional image data by performing a scanning action with a single element transducer. Moreover, it is also possible to use the present invention in cases where three dimensional image data is obtained by performing a scanning action of a transducer or a two dimensional array transducer.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-168161, filed on Jul. 27, 2010, which is hereby incorporated by reference herein in its entirety.

The invention claimed is:

1. An image information obtaining apparatus, comprising:
   a light source;
   a transducer configured to convert an acoustic wave into an electrical signal;
   a signal processing unit configured to obtain image data, using the electrical signal; and
   a memory which stores a reference acoustic signal,
   wherein
   said transducer is configured to output an object acoustic signal by detecting an acoustic wave generated when an object is irradiated with light from said light source,
   said memory stores the reference acoustic signal which is outputted from said transducer by detection of an acoustic wave generated when a phantom, which simulates the object and is located at a position where the object is to be located, is irradiated with light from said light source,
   said signal processing unit is configured to:
      obtain an intensity of a signal corresponding to the acoustic wave generated from a surface of the object, out of the object acoustic signal;
      obtain an intensity of a signal corresponding to the acoustic wave generated from a surface of the phantom, out of the reference acoustic signal;
      obtain a correction coefficient based on a result of comparing between the intensity of the signal corresponding to the acoustic wave generated from the surface of the object and the intensity of the signal corresponding to the acoustic wave generated from the surface of the phantom; and obtain a subtraction signal between the reference acoustic signal and the object acoustic signal which are corrected by using the correction coefficient, and obtain image data using the subtraction signal.

2. The image information obtaining apparatus according to claim 1, wherein the phantom has acoustic parameters and optical parameters substantially the same as the object.

3. The image information obtaining apparatus according to claim 1, wherein a light scattering coefficient of the phantom is no less than 0.45 mm$^{-1}$ and no more than 2.8 mm$^{-1}$, a light absorption coefficient of the phantom is no less than 0.001 mm$^{-1}$ and no more than 0.03 mm$^{-1}$, and an acoustic impedance of the phantom is no less than 1.5×10$^6$ kg/m$^2$ sec and no more than 1.6×10$^6$ kg/m$^2$ sec.

4. The image information obtaining apparatus according to claim 1, wherein a light scattering coefficient of the phantom is no less than 0.45 mm$^{-1}$ and no more than 1.2 mm$^{-1}$, a light absorption coefficient of the phantom is no less than 0.005 mm$^{-1}$ and no more than 0.015 mm$^{-1}$, and an acoustic impedance of the phantom is no less than 1.5×10$^6$ kg/m$^2$ sec and no more than 1.6×10$^6$ kg/m$^2$ sec.

5. The image information obtaining apparatus according to claim 1, wherein the light source emits light in a wavelength range of no less than 700 nm and no more than 1100 nm.

6. The image information obtaining apparatus according to claim 1, wherein said signal processing unit is configured to obtain the correction coefficient such that a difference between the intensity of the signal corresponding to the acoustic wave generated from the surface of the object and the intensity of the signal corresponding to the acoustic wave generated from the surface of the phantom is reduced.

7. The image information obtaining apparatus according to claim 1, wherein said transducer is arranged on a side of an irradiated surface of the object.

8. The image information obtaining apparatus according to claim 7, further comprising an acoustic matching member which is arranged between the object and the transducer and has an acoustic impedance between that of the object and the transducer,
wherein said light source irradiates the object with light through said acoustic matching member.

9. An image information obtaining apparatus, comprising:
a light source;
a transducer configured to convert an acoustic wave into an electrical signal;
a signal processing unit configured to obtain image data, using the electrical signal;
a memory which stores reference image data,
wherein
said transducer is configured to output an object acoustic signal by detecting an acoustic wave generated when an object is irradiated with light from said light source,
said memory stores the reference image data which is obtained based on an acoustic wave generated when a phantom, which simulates the object and is located at a position where the object is to be located, is irradiated with light from said light source, and
said signal processing unit is configured to:
obtain object image data using the object acoustic signal,
obtain an intensity of image data corresponding to the acoustic wave generated from a surface of the object, out of the object image data;
obtain an intensity of image data corresponding to the acoustic wave generated from a surface of the phantom, out of the reference image data;
obtain a correction coefficient based on a result of comparing between the intensity of the image data corresponding to the acoustic wave generated from the surface of the object and the intensity of the image data corresponding to the acoustic wave generated from the surface of the phantom; and
obtain a subtraction image data between the object image data and the reference image data, which are corrected by using the correction coefficient.

10. The image information obtaining apparatus according to claim 9, wherein the phantom has acoustic parameters and optical parameters substantially the same as the object.

11. The image information obtaining apparatus according to claim 9, wherein a light scattering coefficient of the phantom is no less than 0.45 mm$^{-1}$ and no more than 2.8 mm$^{-1}$, a light absorption coefficient of the phantom is no less than 0.001 mm$^{-1}$ and no more than 0.03 mm$^{-1}$, and an acoustic impedance of the phantom is no less than 1.5×10$^6$ kg/m$^2$ sec and no more than 1.6×10$^6$ kg/m$^2$ sec.

12. The image information obtaining apparatus according to claim 9, wherein a light scattering coefficient of the phantom is no less than 0.45 mm$^{-1}$ and no more than 1.2 mm$^{-1}$, a light absorption coefficient of the phantom is no less than 0.005 mm$^{-1}$ and no more than 0.015 mm$^{-1}$, and an acoustic impedance of the phantom is no less than 1.5×10$^6$ kg/m$^2$ sec and no more than 1.6×10$^6$ kg/m$^2$ sec.

13. The image information obtaining apparatus according to claim 9, wherein the light source emit light in a wavelength range of no less than 700 nm and no more than 1100 nm.

14. The image information obtaining apparatus according to claim 9, wherein said signal processing unit is configured to obtain the correction coefficient such that a difference between the intensity of the image data corresponding to the acoustic wave generated from the surface of the object and the intensity of the image data corresponding to the acoustic wave generated from the surface of the phantom is reduced.

15. The image information obtaining apparatus according to claim 9, wherein said transducer is arranged on a side of an irradiated surface of the object.

16. The image information obtaining apparatus according to claim 15, further comprising an acoustic matching member which is arranged between the object and the transducer and has an acoustic impedance between that of the object and the transducer,
wherein said light source irradiates the object with light through said acoustic matching member.

17. A control method for an image information obtaining apparatus having a light source, a transducer configured to convert an acoustic wave into an electrical signal, a memory, and a signal processing unit, wherein the memory stores a reference acoustic signal which is outputted from the transducer by detection of an acoustic wave generated when a phantom, which simulates an object and is located at a position where the object is to be located, is irradiated with light from the light source, the control method comprising:
a step of irradiating the object with light from the light source;
a step of detecting by the transducer an acoustic wave generated from the object which has absorbed light, and storing a signal outputted from the transducer in the memory as an object acoustic signal;
a step of obtaining by the signal processing unit an intensity of a signal corresponding to the acoustic wave generated from a surface of the object, out of the object acoustic signal;

a step of obtaining by the signal processing unit an intensity of a signal corresponding to the acoustic wave generated from a surface of the phantom, out of the reference acoustic signal;

a step of obtaining by the signal processing unit a correction coefficient based on a result of comparing between the intensity of the signal corresponding to the acoustic wave generated from the surface of the object and the intensity of the signal corresponding to the acoustic wave generated from the surface of the phantom;

a step of obtaining by the signal processing unit a subtraction signal between the reference acoustic signal and the object acoustic signal, which are corrected by using the correction coefficient; and a step of obtaining by the signal processing unit image data using the subtraction signal.

18. A control method for an image information obtaining apparatus having a light source, a transducer configured to convert an acoustic into an electrical signal, a memory, and a signal processing unit, wherein the memory stores reference image data which is obtained based on an acoustic wave generated when a phantom, which simulates an object and is located at a position where the object is to be located, is irradiated with light from the light source, the control method comprising:

a step of irradiating the object with light from the light source;

a step of acquiring by the transducer an object acoustic signal by acquiring an acoustic wave, generated when the object is irradiated with light from the light source;

a step of obtaining by the signal processing unit object image data using the object acoustic signal;

a step of obtaining by the signal processing unit an intensity of image data corresponding to the acoustic wave generated from a surface of the object, out of the object image data;

a step of obtaining by the signal processing unit an intensity of image data corresponding to the acoustic wave generated from a surface of the phantom, out of the reference image data;

a step of obtaining by the signal processing unit a correction coefficient based on a result of comparing between the intensity of the image data corresponding to the acoustic wave generated from the surface of the object and the intensity of the image data corresponding to the acoustic wave generated from the surface of the phantom; and a step of obtaining by the signal processing unit subtraction image data between the reference image data and the object image data, which are corrected by using the correction coefficient.

* * * * *